United States Patent [19]

Brown et al.

[11] Patent Number: 5,062,711
[45] Date of Patent: Nov. 5, 1991

[54] METHOD AND APPARATUS FOR INSPECTING WORKPIECES

[75] Inventors: Derek A. Brown, Buckinghamshire; John N. Worth, Bedford; Brian F. Santaniello, Staffordshire, all of England

[73] Assignee: W. R. Grace & Co.-Conn., New York, N.Y.

[21] Appl. No.: 434,731

[22] Filed: Nov. 13, 1989

[30] Foreign Application Priority Data

Nov. 23, 1988 [GB] United Kingdom ................. 8827325
Jun. 9, 1989 [GB] United Kingdom ................. 8913279

[51] Int. Cl.⁵ ......................................... G01N 21/88
[52] U.S. Cl. ..................... 356/394; 356/237; 356/426; 356/445; 156/69; 209/587
[58] Field of Search ........ 356/237, 394, 426, 445–448; 156/69; 209/524, 529, 587

[56] References Cited

U.S. PATENT DOCUMENTS

| | | | |
|---|---|---|---|
| 2,793,746 | 5/1957 | Meyer et al. | 209/111 |
| 2,803,343 | 8/1957 | Dodge | 209/111 |
| 3,395,278 | 7/1968 | McDivitt | 250/83.3 |
| 3,983,388 | 9/1976 | Gugliotta | 250/223 |
| 4,017,194 | 4/1977 | Conroy et al. | 356/240 |
| 4,029,958 | 6/1977 | Wright | 250/223 |
| 4,037,724 | 7/1977 | Schultz et al. | 209/111.7 |
| 4,072,426 | 2/1978 | Horn | 356/212 |
| 4,165,939 | 8/1979 | Woodrow et al. | 356/394 |
| 4,264,202 | 4/1981 | Gugliotta et al. | 356/241 |
| 4,521,807 | 6/1985 | Werson | 358/106 |
| 4,542,296 | 9/1985 | Kleinnibbelink | 250/359.1 |
| 4,668,983 | 5/1987 | Werson | 358/106 |
| 4,728,186 | 3/1988 | Eguchi et al. | 356/71 |
| 4,753,530 | 6/1988 | Knight et al. | 356/73 |
| 4,766,551 | 8/1988 | Begley | 364/498 |
| 4,770,530 | 9/1988 | Aken et al. | 356/323 |
| 4,793,710 | 12/1988 | Sapko et al. | 356/446 |
| 4,873,432 | 10/1989 | Alderman | 250/227 |

FOREIGN PATENT DOCUMENTS

| | | | |
|---|---|---|---|
| 0047612 | 3/1982 | European Pat. Off. | |
| 0111377 | 6/1984 | European Pat. Off. | |
| 0043484 | 4/1977 | Japan | 356/445 |
| 0201241 | 10/1985 | Japan | 356/237 |
| 785223 | 10/1957 | United Kingdom | |
| 1075152 | 7/1967 | United Kingdom | |
| 1292308 | 10/1972 | United Kingdom | |
| 2155625 | 9/1985 | United Kingdom | |
| 2178530 | 2/1987 | United Kingdom | |

OTHER PUBLICATIONS

Translation of Japanese Kokai Patent No. 61-271441, publication date 12-1-1986; Inventors-Kamakura et al.

Primary Examiner—F. L. Evans
Attorney, Agent, or Firm—John D. Hubbard; William L. Baker

[57] ABSTRACT

The apparatus and method disclosed rely on the observation of a strip of a rotatable circular can end to be lined with gasketing composition, and the scanning head further includes a proximity detector responsive to the positioning of the can end adjacent the scanning head and connected to trigger initiation of a "scanning window" when a can end arrives concentrically in the lining chuck at the lining station, and to discontinue the "scanning window" when the can end and chuck begin to descend on departure of the can end for onward transport. The scanning operation is totally independent of time and therefore of the adjustable speed of operation of the can end lining machine.

15 Claims, 4 Drawing Sheets

METHOD AND APPARATUS FOR INSPECTING WORKPIECES

The present invention relates to an improved method of and apparatus for inspecting workpieces, in particular for optical inspection of workpieces passing an inspection station either during or after manufacture.

BACKGROUND OF THE INVENTION

One application for the present invention is the optical examination of the gasket being formed on a container closure which is presented to an inspection station, and then moved, e.g. rotated, at the inspection station to allow a single scanning head to scan a gasket strip, e.g. a circular track, on the container closure, and then advanced from the inspection station and followed by a further such closure. The optical examination of the container closure may, for example, be for the purposes of inspecting the completeness of a sealing gasket formed in the container closure which may, for example, be a bottle or jar closure, a can end, or a drum or pail cover.

However, the invention is not to be limited to use with circular workpieces because it is well known for container closures such as can ends to have an other than circular form (for example rectangular) and to be provided with a gasket over a non-circular peripheral portion adjacent its perimeter.

It is known to inspect circular closures optically for the purposes of confirming the presence and/or continuity of an annular gasket formed near the perimeter of the closure. The closures, for example can ends or bottle or jar caps, are presented in rapid succession to the inspection station, which may also be the lining station, and are to be examined once they are in position on a rotary chuck which holds each can end while it is being rotated to bring the entire length of the peripheral gasket region of the closure past an optical scanning head. However, it is important to define when the scanning operation is to be activated and to cease, because during scanning it is intended that the container closure or other workpiece be held so that its zone passing the optical scanning head presents a constant optically observed quality, for example a constant reflectance to indicate the presence of a gasket material. In the case of gasketing can ends, an ungasketed can end or a portion on which the gasket may be discontinuous, will have a high reflectance value indicating the lack of reflection-attenuating gasketing material whereas the presence of the gasket will give rise to a reflectance value of a predetermined range less than that encountered with an ungasketed can end but above a signal value which may be encountered in the case of a fault in the gasket (for example the presence of a dark impurity particle) or a discontinuity of the can end.

It is known in such inspection equipment to initiate the scanning operation once the container closure is in place on the rotatable chuck, and to define a scanning window in terms of a time delay terminating when it is expected that the scanning rotation of the container closure will have been completed, and before onward advance of the container closure from the inspection station begins.

We have found that the traditional method of counting the time elapsed from the start of the scanning operation to define the end of the "scanning window" has the disadvantage that the timing is specific to the design of the closure lining apparatus with which the inspection equipment is used, and when the machine speed is altered it is necessary to compensate by changing the count value of the clock which defines the width of the "scanning window". Furthermore, it is also frequently the case that the instant of the start of the "scanning window" is in need of compensation when the machine speed is changed.

SUMMARY OF THE INVENTION

It is an object of the present invention to provide an optical inspection system which allows the operating speed of the transport system for the workpieces to be varied without the need for readjustment of the workpiece inspection system. With such an apparatus and method it is then possible to provide a totally independent workpiece inspection system which relies on proprietary workpiece transport means to which the inspection equipment can be readily attached, and without the need for any compensation for the operating speed of the transport equipment. The transport equipment used may, for example, be a machine for lining can ends, where the optical inspection equipment can desirably be incorporated at the can end lining station to inspect the can end while the lining gasket is being formed.

According to one aspect of the present invention we provide a method of inspecting workpieces comprising holding the workpiece at an inspection station, illuminating a region of the workpiece and observing the reflected illumination from that region for evaluation of the reflectance properties of the workpiece, detecting the position of the workpiece to initiate a scanning phase only when the workpiece is in a predetermined position relative to the observation head, scanning said illuminated region along a closed path over the surface of said workpiece for at least one complete circuit of said closed path to define the scanning phase, discontinuing the scanning phase when the workpiece leaves said predetermined position, and processing the signals derived from the observation head only during the scanning phase for activating a signal corresponding to acceptability in the case of a workpiece corresponding to certain predefined conditions and activating a rejection signal in the case of a workpiece which does not correspond to the predefined conditions.

According to a second aspect of the present invention we provide apparatus for inspecting workpieces, comprising: an optical observation head; means for detecting the arrival of a workpiece in a predetermined position spaced from said observation head; means responsive to the signal of said position-detecting means for initiating a temporal scanning window in which the signals of said observation head are processed to discriminate between acceptable workpieces and non-acceptable workpieces; means for determining departure of the workpiece from said predetermined position relative to the observation head for discontinuing the scanning window; drive means for causing relative movement between said observation head and a said workpiece to ensure scanning over at least one circuit of a closed path on the surface of said workpiece; and means controlled by said scanning window initiation and discontinuing means for processing the signals of said observation head only within said scanning window, and for determining whether said signals correspond to a pre-programmed set of "acceptance" conditions which correspond to generation of a "workpiece acceptable" signal and for discriminating from other signals which do not satisfy said conditions and correspond to a "workpiece non-acceptable" condition.

Although the means for discontinuing the temporal scanning window are preferably responsive to the same position detecting means as that used for initiating the scanning window, it is also possible for the deactivating means to comprise means for detecting decay of the signal from the scanning means upon termination of the scanning relative movement as the workpiece begins to leave the scanning position.

BRIEF DESCRIPTION OF THE DRAWINGS

In order that the present invention may more readily by understood the following description is given, merely by way of example, with reference to the accompanying drawings in which.

DETAILED DESCRIPTION

Figure 1:
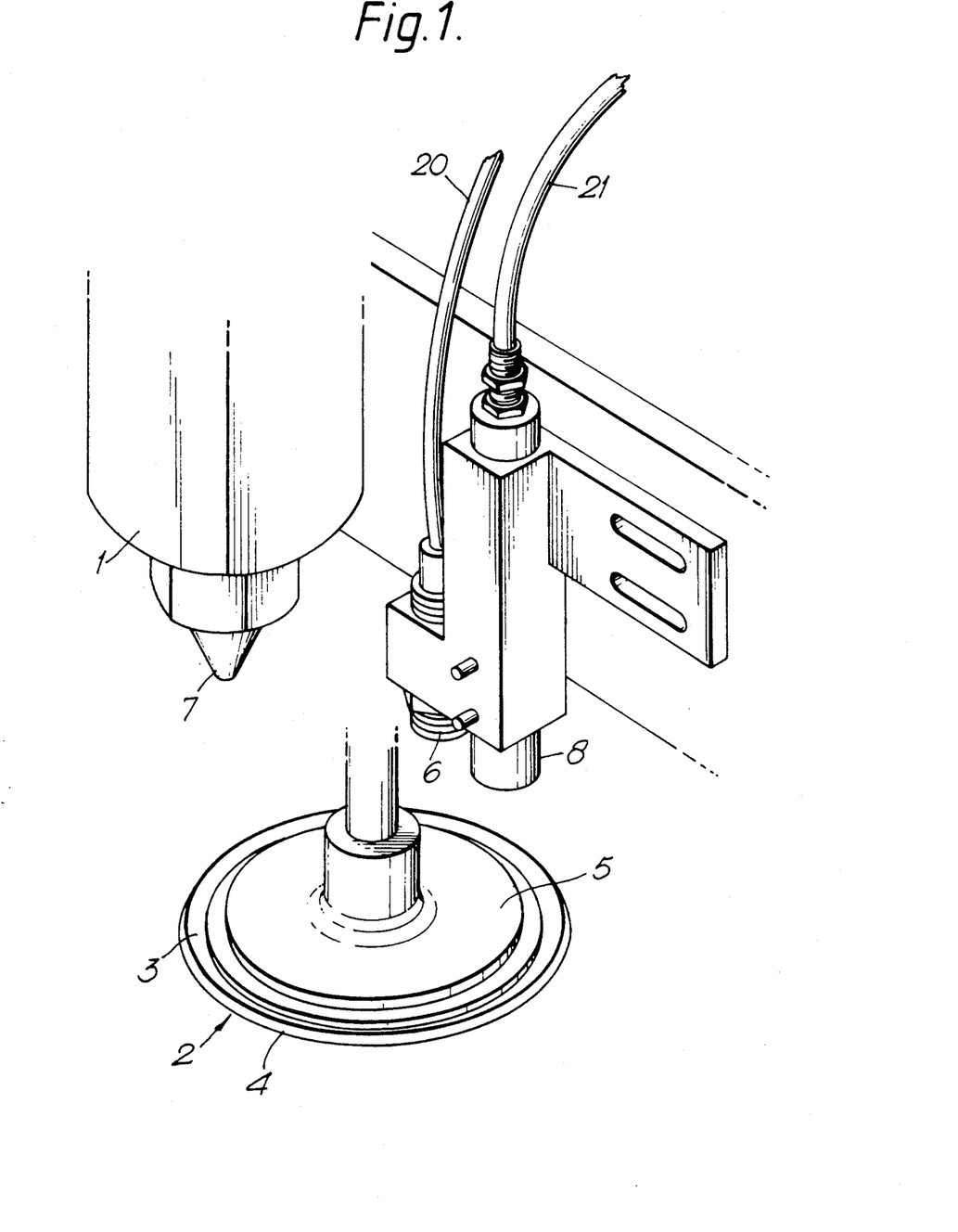
FIG. 1 is a perspective view of a workpiece inspection station in accordance with the present invention.

FIG. 1 shows a perspective view of a can end lining machine, namely a version of the apparatus of the present invention in which the workpieces are the circular end plates of cylindrical cans which require to receive gaskets to seal the periphery of the can end to the respective end of the cylindrical wall of a can being formed.

In FIG. 1 there is shown a dispensing gun 1 which drops liquid lining composition on to the can end 2 in a peripheral region 3 just inboard of the curl 4 at the perimeter of the can end. During this lining operation the can end 2 is being rotated at high speed between a chuck 20 (FIG. 5) underneath the can end and a hold down pad 5 above the can end.

Figure 5:
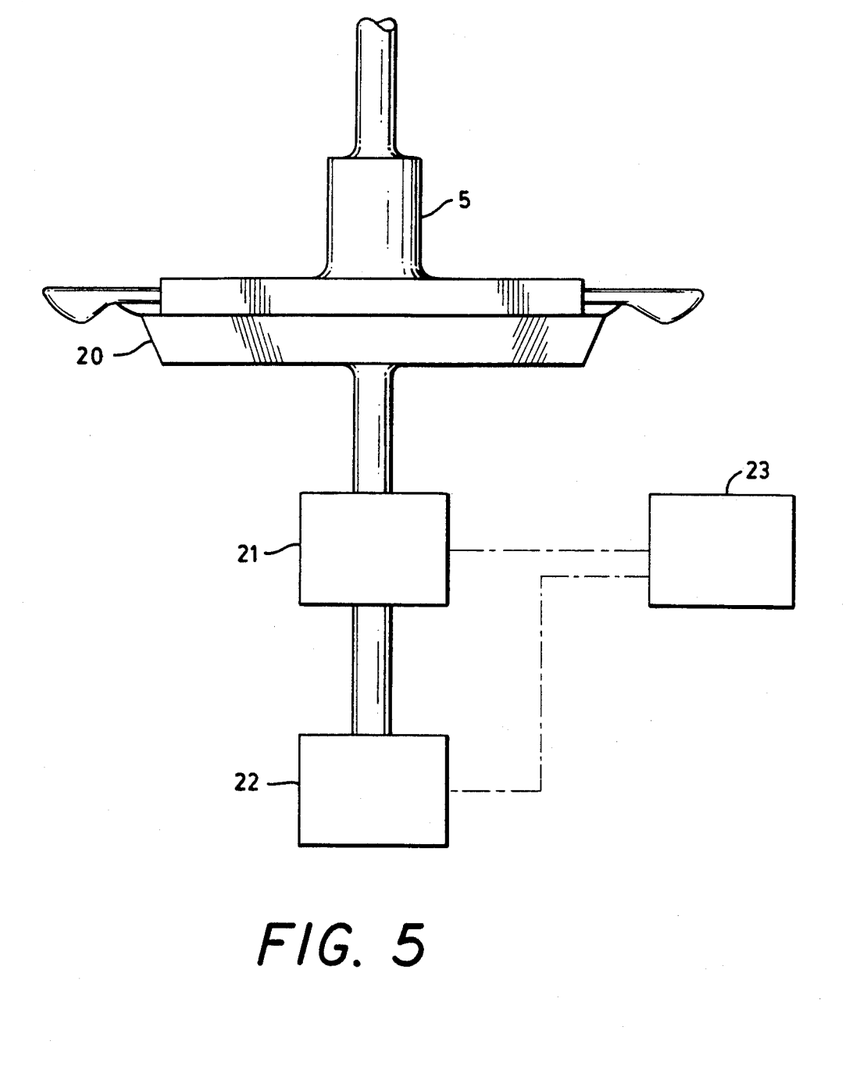
FIG. 5 shows a schematic elevational view of the can end drive chuck and the drive means therefore.

FIG. 5 also shows a rotational drive means 21 driven from the main drive of the can end lining machine, for rotating the chuck 20, and also vertical drive means 22 driven by the same main drive of the can end lining machine for lifting and lowering the chuck to grasp and release, respectively, a can end to be inspected. The machine main drive is able to be driven at a variable speed adjusted by adjustment means 23 which thus allow the speed of operation of the rotational drive means 21 and the vertical drive means 22 to be varied.

For a lining operation the underneath chuck rises and the can end 2 thus becomes gripped between the chuck and the hold down pad 5 and is lifted so as to come closer to a proximity detector 6, in this case an inductive detector. At the same time the can end is closer to the nozzle 7 of the gun 1, and is furthermore positioned closely beneath an optical sensing head 8 which monitors the application of lining composition to form the gasket such a can lining device is shown in U.S. Pat. No. 4,605,351.

The can end becomes lifted by a distance of the order of 9 mm prior to the lining and inspection operation, and the proximity detector 6 is accurate to within a half millimeter. It is thus possible to provide an electrical signal at precisely the instant at which the can end has lifted far enough to reach its lining and inspection position.

When in this "inspection" position the can end has its gasket region 3 observed by the optical observation head 8 which emits a focused beam of modulated light (which may for example be red) such that the beam is focused at a point on the gasket region 3.

The optical sensing system employs two sets of optical fibres which have first ends arranged together in the optical sensing head 8. One of the sets of optical fibres has its further ends adjacent a source of the modulated light whereas the other has its further ends alongside a detector of the same modulated light. The same observation head 8 thus emits the scanning light onto the can end and detects radiation reflected back.

Figure 2:
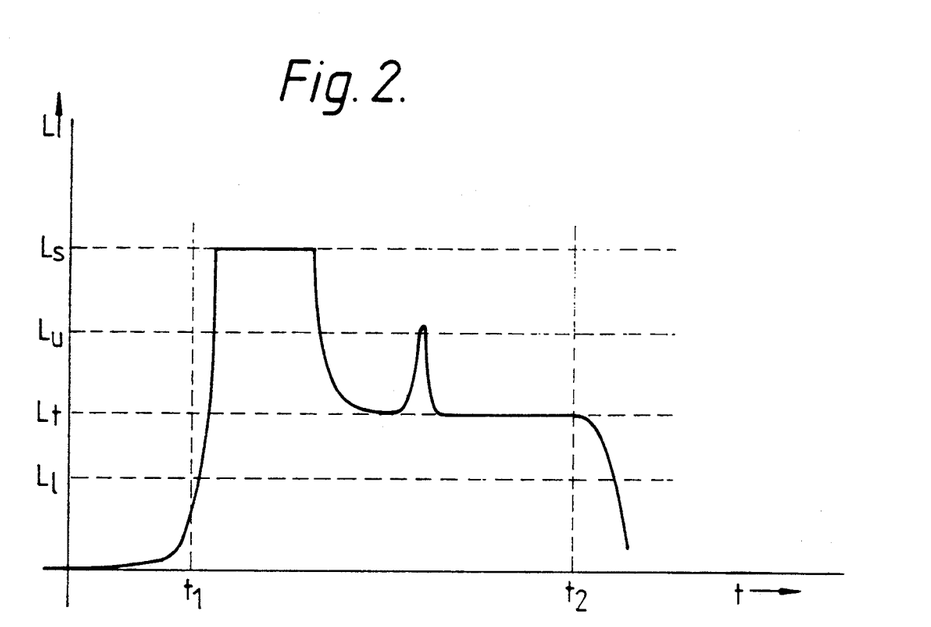
FIG. 2 is a plot of the level of the signal due to the reflected light from the optical observation head when an unacceptable workpiece is present.
Figure 4:
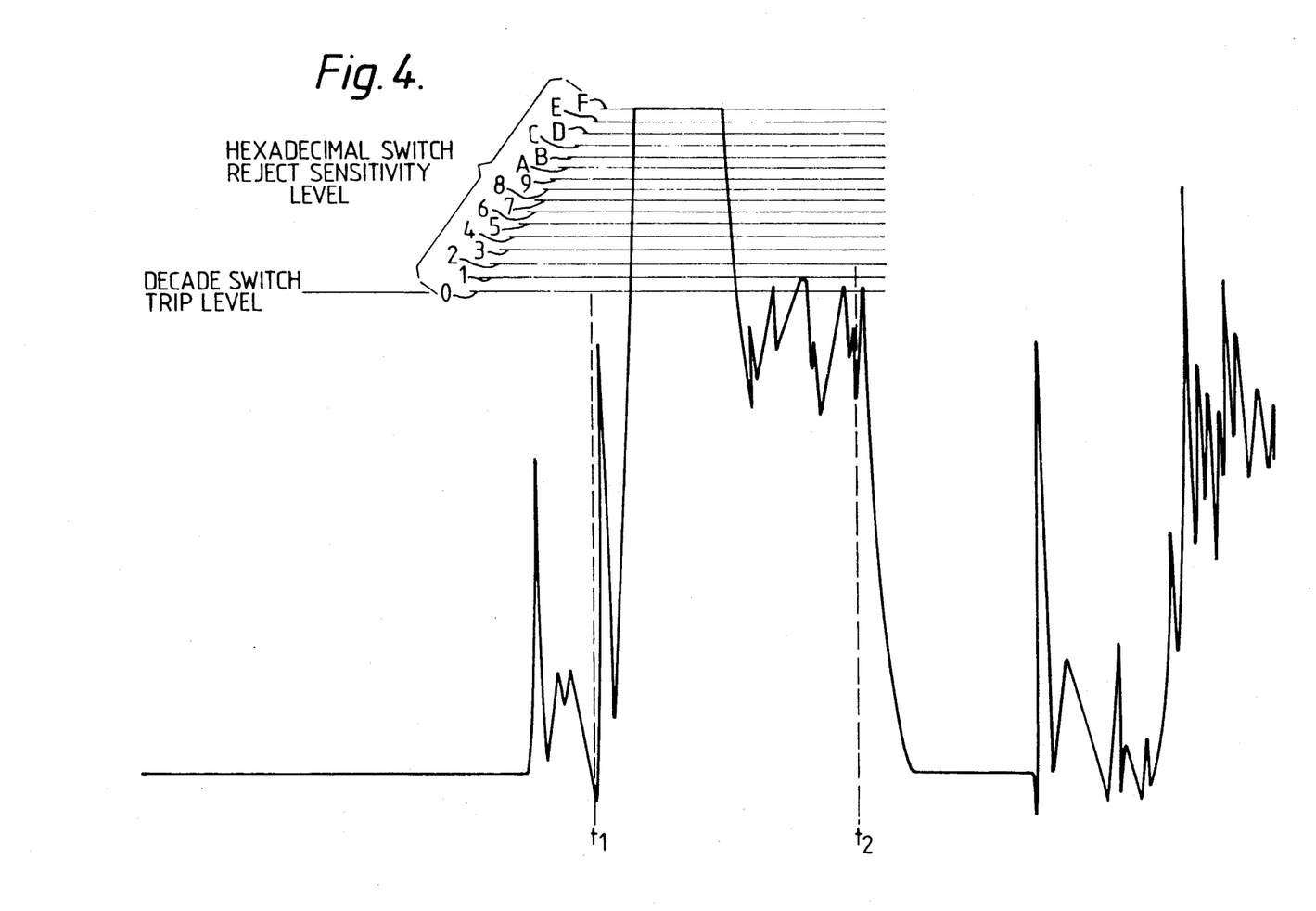
FIG. 4 is the trace obtained from a pen recorder plot of the actual signal strength which is shown in idealized form in FIG. 2, but when an acceptable workpiece is present.

During the operations of feeding an unlined can end to the chuck and hold down pad 5, and the operation of advancing that can end, after lining, to a downstream processing station, various different reflectance situations, two sequences of which are shown in FIGS. 2 and 4, will be observed by the observation head 8.

Firstly, before arrival of the can end, the components of the machine will be well below the focal point of the observation head and the emitted light may in the main be lost rather than being reflected back. The signal could therefore be of very low strength.

As the periphery of the unlined can end comes in front of the optical observation head 8 the signal will rise because of the high reflectance of the metal surface of the unlined can end. Then, as the lining gun 1 begins to dispense lining composition to form a gasket near the can end periphery, the gasket area being scanned will become less reflective but will nevertheless have a distinct reflectance value which is less than that relevant to the unlined metal of the can end.

On the assumption that the can end has a perfect gasket formed in it, the gasket will give a constant predetermined reflectance value during rotation of the can end and application of the lining gasket; then upon termination of the inspection phase the can end at instant $t_2$ will move on and the signal will thus once again die away to a very low value, although possibly first of all rising to the "unlined metal" condition as the periphery of the can end with its "curl" is caused to pass the scanned field.

This excursion of the signal can be appreciated from FIG. 2 where the time instant $t_1$ occurs during the rising front of the signal towards a saturation value $L_s$ during the positioning of the unlined can end on the chuck. This instant $t_1$ is determined by the proximity detector 6 and corresponds to the instant when the can end has risen with the chuck and hold down pad to its "lining" position. The signal will however then continue to rise to the saturation value $L_s$ despite the fact that the scanning operation has now started.

The scanning programme will expect the signal to stay at least as great as, or in excess of, the saturation level $L_s$ for a given time during which the unlined can end is rotating and maybe even while the start of the lined strip of the can end is moving round towards the observation head 8 (which can be seen in FIG. 1 as being substantially 180° out of phase with the gun 1 in that they are diametrically opposite one another).

The scanning programme also requires the signal to drop below the saturation level $L_s$ at some later time the timing of which is not critical, and to pass down through an upper trip level $L_u$ the purpose of which will be described below. In fact the signal continues to descend to a normal level $L_t$ at which the reflectance of the lined can end has a substantially constant value which should ideally be held for the remainder of the duration of the "scanning window" during which the inspection equipment is recording the presence of a uniform gasket.

At a later stage the can end lining machine will begin to drop the can end 2 from the lining and inspection position towards a position in which the chuck and the hold down pad can release that lined can end for onward transport to a subsequent handling station. As the can end starts to descend away from the lining and inspection position, the proximity detector creates a second signal on line $t_2$ to mark the end of the "scanning window". In practice the signal will then drop from the normal level $L_t$ towards and through a lower level $L_1$.

The very idealized drawing of FIG. 2 shows one fault in the gasket in that there is, in the plateau region at normal level $L_t$, an upward spike which simulates the temporary increase of reflectance signal which might result if the gasket had a discontinuity in it.

The rejection of the can end responsible for the "signature" on FIG. 2 is caused as a result of the attainment of this spike through the upper threshold level $L_u$, given a sufficiently short response time of the circuit.

The purpose, therefore, of the upper trip level $L_u$ is to provide a maximum limit on the acceptable signal after the descent of the signal from the even higher saturation limit $L_s$.

Indeed, as will be described later, the normal level $L_t$ and the upper trip limit $L_u$ are both adjustable on site without the need for external electrical equipment to check calibration of the equipment.

If, conversely, there had been a downward dip in the signal from the plateau at normal level $L_t$, then if this had been more than a certain duration depending on the response time of the circuit and an amplitude preset by the designer it could represent a change of contrast in the gasket or end and would cause an "unacceptable end" signal.

The equipment operating in accordance with the present invention has the advantage that the "scanning window" is not determined by a fixed time counted from a start of the "scanning window", but is instead defined by two temporally spaced instants between which the scanning operation is carried out.

For an acceptable gasket, the signal must rise through upper trip limit $L_u$ after time instant $t_1$.

Subsequently the signal L should descend from the upper trip level $L_u$ back down to a normal level $L_t$ which it should hold without excessive increase or decrease until the end of the "scanning window". The "signature" shown in FIG. 2 would thus be responsible for rejection of a closure by virtue of the fact that the lower plateau at normal level $L_t$ is not maintained in view of the upward spike from $L_t$ to a value above the upper trip limit $L_u$.

As mentioned above, the trace shown in FIG. 2 represents that of a can end having a faulty gasket due to a discontinuity in the gasket corresponding to the sudden upward spike before the "scanning window" shut off point $T_2$. On the other hand, the trace shown in FIG. 4 represents that of an acceptable gasket in that although there is also an upward spike after descent from the saturation level and before "scanning window" shut off point $t_2$, this spike does not exceed the trip level $L_t$ of FIG. 2 ("hexadecimal switch trip level" 0 of FIG. 4) and is hence within acceptable limits in that that signal magnitude is still consistent with adequate gasket thickness.

The circuit of the inspection equipment has a facility for disabling the requirement for the signal first of all to reach saturation level $L_s$ (which it does when presented with an unlined can end which then becomes subject to the plateau at normal level $L_t$ after a distinct period at saturation level $L_s$), so that the signal can remain at the plateau at normal level $L_t$ without that first excursion up to the saturation level $L_s$ in the event of requiring the inspection equipment to monitor prelined can ends.

The purpose of the facility normally in the programme for rejecting a can end which does not attain the upper trip level $L_u$ is to guard against the lining equipment being presented with a prelined can end during "on-line" can end inspection. This facility for "off-line" inspection of pre-lined can ends can be useful in certain circumstances.

The programme is also preferably designed to give a reject signal if, in the course of a normal "on-line" inspection operation, the observation head signal does not exceed the lower level $L_1$ after instant $t_1$, or the proximity detector does not indicate proximity of the can end 2 to the detector 6 while the reflectance signal is above the upper trip level $L_u$. There is thus a cross check between these two detectors 6 and 8 to ensure that both are operating correctly. Otherwise an alarm is initiated.

By using modulated light, it is possible to avoid the need for shielding of the sensor and hence it is made much more straightforward to focus the beam of radiation at a spot on the can end gasket strip.

An alternative possibility for detecting arrival of the workpiece such as the can end in its inspection position would be to have some position switch responsive to operation of the mechanism of the workpiece transport system, for example the drive to the chuck and hold down pad in the apparatus of FIG. 1. However, we consider it is preferable to rely on a proximity sensor as this allows the inspection equipment to be attached as a retrofit to any existing apparatus in which the workpiece are forwarded to, and advanced from, an inspection station.

The inspection station could, of course, be elsewhere than at the lining station of a can end lining machine, although the installation of the inspection equipment at the lining station is particularly advantageous because this is a point where the circular can end must of necessity be rotating about a stationary axis in order to facilitate both the application of the lining material, and as a side advantage, the scanning for inspection purposes.

Figure 3:
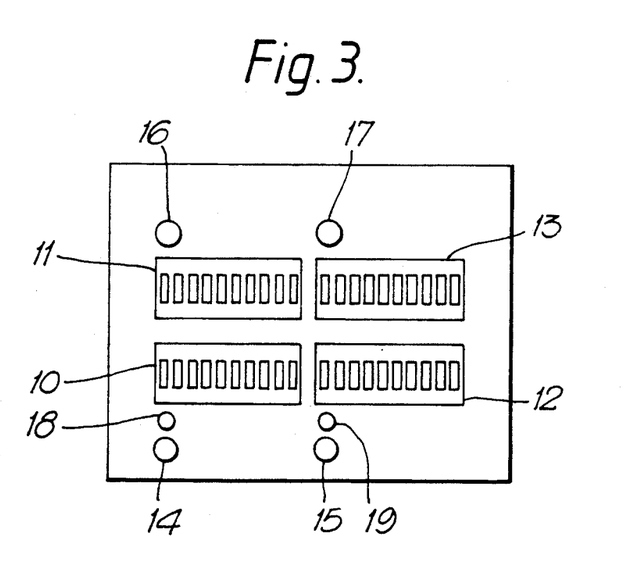
FIG. 3 is a view of part of the control panel of the inspection equipment.

FIG. 4 shows a pen recorder trace of the signal L of FIG. 2, actually measured on the apparatus shown in FIGS. 1 and 3. FIG. 4 also shows the increments (0, 1, 2, . . . D, E, F) of a hexadecimal switch whose range extends from the normal level ($L_t$ in FIG. 2) to the saturation level ($L_s$ in FIG. 2).

As can be seen from the left hand part of FIG. 4, the signal is initially low as there is no can end at the lining station. During approach of the can end to be inspected there are two upward spikes which are thought to have been caused by optical observation of the can end transfer bars feeding the can end to the lining chuck. Immediately after the second spike the signal rises rapidly through the level 0 marked "decade switch trip level"

which corresponds to the normal signal level $L_t$ of FIG. 2, and up to the saturation level $L_s$.

The equipment in accordance with the present invention uses a particularly simple system for setting up the switches to define the levels $L_t$ and $L_u$.

As shown in FIG. 3, the control panel includes a first pair of bar graph indicators 10 and 11, and a second pair of such indicators 12 and 13. These constitute two distinct channels of the equipment which can either be used to monitor different aspects or different positions on a single lining station or to scan simultaneously each of two lining stations each requiring one of the two scanning channels of the equipment.

Although, in the preferred form of the present invention, two separate channels are incorporated it is also possible for three or more such channels to be incorporated in the same unit. With two such channels, as indicated above, it is possible to observe different parts of the gasket track, for example by arranging one of the detectors 8 to scan the outer perimeter of the gasket strip and the other to scan the inner perimeter, in order to detect any ragged edges to the gasket at either the inner or the outer perimeters.

Another possibility would be for there to be the same two channels observing the gasket track and for a third channel to be watching the curl at the outer perimeter of the can end to ensure that the curl is correctly formed. Yet a further possibility would be for there to be at least one channel observing the gasket track on the top of the can end and for a further channel observing the outside of the curl to ensure that no compound spills over onto the other side of the can end.

The two bar graphs 10 and 12 are reference bar graphs which, during a setting-up cycle of the equipment, indicate the desired normal level $L_t$; on the other hand, the bar graphs 11 and 13 indicate the reflectance level of the gasket on the respective channel, and the desired and actual values are to be set in relation to one another, e.g. equalised, by adjustment of decade switches controlling the two other bar graphs 11 and 13 to illuminate the same number of bars on graphs 11 and 13 as on graphs 10 and 12, respectively.

The signal on each of the bar graphs 10 and 12 is obtained by positioning a prelined can end 2 of known gasket quality in the appropriate chuck and then winding that chuck manually for lifting movement into the "inspection" position just below the optical observation head 8 and proximity detector 6, and then adjusting the sensitivity the reflectance signal of the thus lined can end to provide an "acceptable reflectance" signal which corresponds to, say, 3 bars illuminated in the bar graph indicator 10 or 12. To do this, for each channel, the sensitivity control 18 or 19 shown in FIG. 3 is then adjusted.

Then the decade switches 14 and 15 are adapted to bring the bar graph indicators 11 and 13 into a desired relationship (e.g. equality) in relation to the bar graphs 10 and 12.

The above-mentioned hexadecimal switches 16 and 17 define sixteen increments of signal strength above and starting from the normal level $L_t$ defining an effective range up to the saturation level $L_s$ for the inspection equipment.

The initial presentation of a quality-controlled lined can end for setting up the equipment provides not only for adjustment of the device for the correct sensitivity with the intended lining composition (and hence also to enable adjustment to a different sensitivity when a compound having a different reflectance is used), but also for adjustment of the sensitivity to cope with any slight repositioning of the optical sensing head 8 and the proximity detector 6 relative to the raised "inspection" position of the can end in the chuck.

The sensitivity of the rejection facility is adjusted by selecting an appropriate one of the levels 1, 2, 3, . . . C, D, E of the range of the hexadecimal switches 16, 17 (FIG. 3) and this then defines the upper trip level $L_u$ of FIG. 2. It will of course be appreciated that if the upper trip level $L_u$ is too close to the normal level $L_t$ then virtually every can end will be rejected, including a high number of acceptable ones (as mentioned above), and that equally if the upper trip level $L_u$ is too close to the saturation level $L_s$ (for example by selecting level E of the hexadecimal switch) only ends with areas of gasket missing will be rejected because it is unlikely that any spike resulting from a small fault in the gasket will be high enough to be virtually equal to the saturation level $L_s$. The operator therefore adjusts the hexadecimal switch 16 or 17, to a setting at which from experience he finds that the only can ends which are rejected are faulty, and that there is no noticeable incidence of badly lined can ends passing inspection. This setting will be determined by trial and error and/or empirical prediction, for example by selecting level 8.

It is considered particularly important that with the present invention there is a way of adjusting the sensitivity of the inspection equipment using only a quality-controlled lined can end, and requiring no external calibration apparatus. Furthermore, the particularly convenient calibration system which simply requires the equalization of two adjacent and parallel bar graphs is considered an important practical advantage for operation of the inspection unit.

Other methods of "de-sensitizing" the inspection equipment can be employed, either as alternatives to the above-mentioned sensitivity adjustment or in co-operation with that adjustment.

For example, when the apparatus is set up to reject can ends having a minor fault in the top turn of the lining (which is normally applied during a rotation of more than 360° of arc), then normally that apparatus would equally reject a can end having had such a minor flaw in the earlier-applied part of the lining even if it has been covered by the top layer of lining material applied during the last turn before de-energization of the lining gun solenoid or other control mechanism. However, in practice, such a can end may be perfectly acceptable for its purpose of sealing a cylindrical can.

One way of de-sensitizing the system so that such a can end will be accepted would be to program the system to reject a can end only if small discontinuities (short in terms of the duration of the abnormality of the signal during the observation window) are detected twice during observation. This characteristic relies on the fact that the duration of the can end lining operation will normally exceed the time for one complete rotation of the can end (in order to ensure a continuous gasket) and may even exceed two complete rotations; hence if a fault occurs only once then the can end would be acceptable. For example, if a minor fault is taken as being one where the duration of the signal abnormality is no greater than a threshold duration of, say, 1.5 msec, then such a short abnormality detected during the first rotation will be insignificant if it does not recur during the second rotation. Thus the system could be set up to disregard any short duration fault (with a duration of no more than 1.5 msec) which occurs only once during the observation window. This set up is therefore one in which all longer duration faults (of more than 1.5 msec duration) will result in rejection, and shorter duration faults will only result in rejection if they are seen twice.

Such short duration faults (for example faults of the order of 1 msec or less) could be due to a partial nozzle blockage which then clears for the remainder of the lining operation on that can end. In such a case the first observation of that fault will be recorded in a memory and only when a second observation of a similarly short fault occurs would there be rejection. If a larger (longer than 1.5 msec duration) fault is seen at any time during the scanning window then the can end will be rejected regardless of detection of repeated observation of the fault, so this requirement for repeated observation only applies for short duration faults.

As a refinement of this system, the program may be capable of disregarding all short duration faults other than those which are temporally spaced by an interval equivalent to one turn of the chuck. This "interval responsive" selection may either be applied in the case of all flaw durations or in the case of only shorter duration flaws when any can end having a longer duration flaw will be rejected.

A second way of implementing this form of de-sensitization to disregard flaws in the underlayer would be to program the system to record the signal excursion throughout the scanning window and to count the duration of the scanning window and, upon the termination of the scanning window, to select an observation window lasting only for substantially the last turn of the lining. The system then disregards any observations of flaws carried out within the scanning window but outside the observation window (i.e. during the first fraction of the scanning window corresponding to turns other than the last turn of lining compound application). For example, if it is known that the final turn of the lining is produced only during the last 30% of the total rotation which occurs between arrival of the can end at the lining station and departure of the can end from the lining station, then the program could be such that only faults timed as occurring when the ratio of (i) elapsed time since the start of the scanning window to (ii) the total duration of the scanning window is greater than 0.7 (i.e. those occurring in an interval following the start of the observation operation which is from 70% to 100% of the total duration of the observation operation) would be regarded as effective. Hence effectively the observation window is reduced to correspond to the last 30% of the rotation of the lining chuck between attainment of its raised position and departure from that raised position after lining (i.e. the last 30% of the scanning window). This processing of the signal to identify the last turn will always be valid regardless of the speed of operation of the lining equipment since the ratio of the duration of the last turn to the duration of the total lining rotation operation will be substantially constant regardless of the speed of operation of the machine when the rotation is mechanically driven from the main machine drive; hence speeding up the main machine drive will in turn speed up the rate of rotation and shorten the rotation operation.

The above two variations for de-sensitization purposes are particularly appropriate where the can end is being subjected to "on-line" observation (i.e. observation of the quality of the lining during the lining operation rotation) where the alteration of the machine throughput speed will also affect the speed of observation. When the can ends are subjected to "off-line" observation, it will in practice be more straightforward to run at a constant observation unit speed which is no longer dependent on the throughput speed of the can end lining equipment.

In practice the entire control apparatus will be contained in an explosion-proof casing, preferably having a transparent polycarbonate window enabling the bar graphs to be observed during operation of the inspection apparatus, and some calibration adjustments may be made with the polycarbonate front window removed so that once the equipment has been calibrated and the window replaced, the self-contained unit from which the proximity sensor lead 20 and the optical fiber cable 21 of FIG. 1 originate can then remain sealed and be free from any inadvertent decalibration in use.

It is envisaged that the dispensing gun 1 for the lining compound will be electronically controlled and that there could be some operative connection between the control for the gun 1 and the timing of the "scanning window" $t_1$-$t_2$, but the preferred embodiment of the present apparatus avoids such an interconnection and is therefore equally well able to operate with non-electronically actuated guns, as well as in the "off-line" mode described above.

We envisage that the equipment will usually be constructed as a two-channel system so that spares holding can be facilitated in avoiding the alternative possibilities of single channel and twin channel equipment. Furthermore, this provides a certain amount of additional reliability in that if only one channel is used and that one fails in service, it is possible to disconnect the channel and to employ the other channel without the equipment needing repair.

Although, in the preferred method and apparatus, we use modulated light for scanning it would be possible to work with other radiation such as infra-red.

While the present invention has been described in relation to the preferred embodiments, it would be obvious to one skilled in the art that other variations and modifications may be made in the invention without departing from its true spirit and scope. It is therefore intended in the appended claims to cover all such equivalents, variations and modifications as full within the true spirit and scope of this invention.

What is claimed is:

1. A method of inspecting a workpiece comprising the steps of:
   (a) holding a workpiece at an inspection station,
   (b) illuminating a region of the workpiece and observing by means of an observation head the reflected illumination from that region for evaluation of the reflectance properties of the workpiece,
   (c) detecting the position of the workpiece to initiate a scanning phase only when the workpiece is in a predetermined positioned relative to the observation head, said observation head emitting signals representative of the reflection from said illuminated region,
   (d) scanning the illuminated region along a closed path over the surface of the workpiece for at least one complete circuit of the closed path to define the scanning phase,
   (e) discontinuing the scanning phase when the workpiece leaves the predetermined position; and
   (f) processing the signals derived from the observation head only during the scanning phase for indicating acceptability in the case of a workpiece corresponding to certain predefined conditions and indicating a rejection signal in the case of a workpiece which does not correspond to the predefined conditions; wherein the predefined conditions include change of the reflected illumination from a first level representing an unfinished state of the illuminated region of the workpiece to a second level representing the result of further processing; and wherein a rejection is indicated when one of failure to the change, and a variation from the second level representing poor quality of the further processing, is observed.

2. A method according to claim 1, comprising detecting the position of the workpiece at the start of the scanning phase by means of a proximity sensor.

3. A method according to claim 2, wherein the determination of the end of the scanning phase is achieved by sensing change in a proximity sensor signal indicating departure of the workpiece from its inspection position.

4. A method according to claim 1, wherein said predefined conditions corresponding to acceptance of the workpiece comprise:
   (i) the existence of a signal below a predetermined trip level at the start of the scanning phase,
   (ii) rise of the signal through said predetermined trip level,
   (iii) subsequent attainment of an upper saturation level after the start of the scanning phase, then descent of the signal from the saturation level and down to a value below said trip level before termination of the scanning phase; and
   (iv) the non-existence of any upward signal excursion back through said trip level between said descent and the end of the scanning phase.

5. A method according to claim 4, wherein said acceptance signal conditions further include the non-existence of a downward excursion of the signal below a lower threshold level which is less than said trip level, between said descent and the end of said scanning phase.

6. A method according to claim 1, wherein the illumination is modulated light and the observation is confined to light of the appropriate modulation.

7. A method according to claim 1, wherein the illumination is focused into a spot on the area of the workpiece to be examined.

8. A method according to claim 1, and including the step of calibrating inspection equipment to carry out the inspection method, wherein the calibration operation comprises:
   (a) introducing an acceptable workpiece to an inspection station of the equipment, with the area of the workpiece to be scanned thereby having the desired reflectance characteristics;
   (b) visually displaying a reference signal corresponding to the signal strength observed by scanning the area of the introduced acceptable workpiece;
   (c) visually displaying adjacent the first-mentioned display a signal corresponding to a trip level predetermined by the inspection equipment;
   (d) adjusting the trip level signal to a desired value relative to that of the reference signal provided by the first-mentioned visual display corresponding to the introduced workpiece; and then
   (e) adjusting the sensitivity of the equipment to define an upper threshold level above said trip level such that variations of the detected signal in use of the inspection equipment from the trip level towards said upper threshold level during scanning of the region will not cause display of a "non-acceptance" signal unless the upper level is exceeded.

9. A method according to claim 8, wherein said desired value of the trip level is at least substantially equal to said reference signal.

10. A method according to claim 9, wherein the workpiece is a closure for a container having a side wall to cooperate with said closure, which closure is being lined with gasket material to effect a seal between the closure and the cooperating end of the side wall of a container, and the observation detects the presence of gasketing material which attenuates the reflectance properties.

11. A method of inspecting a workpiece comprising:
   (a) holding the workpiece at an inspection station;
   (b) rotating the workpiece about an axis during a scanning phase;
   (c) illuminating a region of the workpiece which, during the rotation, tracks along a closed path on the surface of the workpiece for a number of circuits which is not necessarily an integer but is greater than unity;
   (d) scanning the illuminated region and detecting changes in the reflected illumination due to changes in the nature of the workpiece surface region, to generate reflectance signals; and
   (e) processing the reflectance signals resulting from the scanning to detect workpiece acceptable conditions and workpiece non-acceptable conditions;
wherein the step of processing the signals includes:
   (i) discriminating between signal excursions having a duration longer than a threshold duration value and signal excursions having a duration shorter than the threshold value; and
   (ii) determining the workpiece acceptable conditions as those in which no shorter duration excursion is repeated during successive circuits of the path.

12. A method according to claim 11, including the steps of (a) defining an observation phase which is shorter than said scanning phase and corresponds to substantially the last complete said circuit of the closed path; (b) considering as non-acceptable a workpiece having any excursion value whose duration exceeds said duration threshold at any stage during the scanning phase; and (c) considering as acceptable any workpieces which do not have any said longer duration excursion at any stage during the scanning and which may or may not have at least one said shorter duration excursion between the start of the scanning phase and the start of said observation phase but which do not have any said shorter duration excursion during the observation phase.

13. A method according to claim 11, and including the steps of considering as non-acceptable any workpiece having a said longer duration excursion and considering as acceptable all other workpieces scanned except for those having more than one said shorter duration excursion.

14. A method according to claim 11, comprising the steps of:
   (a) measuring the total duration of said scanning phase;
   (b) computing the duration of any one circuit of the scanning operation; and
   (c) considering as acceptable any workpieces which have said longer or shorter duration excursions unless they are separated in time by said computed duration of a circuit.

15. A method according to claim 14, comprising considering as non-acceptable all workpieces having any said longer duration excursions.

* * * * *